US009617205B2

(12) United States Patent
Tabirian et al.

(10) Patent No.: US 9,617,205 B2
(45) Date of Patent: Apr. 11, 2017

(54) METHOD OF FABRICATING A LIQUID CRYSTAL POLYMER FILM

(71) Applicants: The United States of America as Represented by the Secretary of the Army, Washington, DC (US); Beam Engineering for Advanced Measurements Co., Orlando, FL (US)

(72) Inventors: Nelson V. Tabirian, Winter Park, FL (US); Sarik R. Nersisyan, Winter Park, FL (US); Brian R. Kimball, Shrewsbury, MA (US); Diane M. Steeves, Franklin, MA (US); Rafael O Vergara, Winter Park, FL (US)

(73) Assignees: Beam Engineering for Advanced Measurements Co., Orlando, FL (US); The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 14/810,589

(22) Filed: Jul. 28, 2015

(65) Prior Publication Data
US 2016/0023993 A1 Jan. 28, 2016

Related U.S. Application Data

(63) Continuation of application No. 14/203,630, filed on Mar. 11, 2014, now abandoned.

(51) Int. Cl.
*B29D 11/00* (2006.01)
*G02F 1/1337* (2006.01)
(Continued)

(52) U.S. Cl.
CPC ...... *C07C 245/08* (2013.01); *B29D 11/00788* (2013.01); *C09B 33/044* (2013.01);
(Continued)

(58) Field of Classification Search
None
See application file for complete search history.

(56) References Cited

U.S. PATENT DOCUMENTS 2,435,616 A * 2/1948 Vittum ................. G03C 7/3335
                                                  430/378
4,956,141 A * 9/1990 Allen ..................... B29C 33/68
                                                  264/297.2
(Continued)

FOREIGN PATENT DOCUMENTS

GB       2209751       *  9/1988
JP       51-109025     *  9/1976
JP       2004-226752   *  8/2004

OTHER PUBLICATIONS

Ichimura et al. "Surface assisted photoalignment control of lyotropic liquid crystals. Part 1. Characterization and photoalignment of aqueous solutions of a water soluble dyes as lyotropic liquid crystals", J. Mater. Chem., vol. 12 pp. 3380-3386 (2002).*

(Continued)

*Primary Examiner* — Martin Angebranndt
(74) *Attorney, Agent, or Firm* — Brian S. Steinberger; Law Offices of Brian S. Steinberger, P.A.

(57) ABSTRACT

A method of fabricating a liquid crystal polymer film includes providing a support substrate having a surface having a shape arranged to define a form of a liquid crystal polymer film to be fabricated; applying a layer of a photoaligning material over the surface of the support substrate, the photoaligning material having an absorption band; exposing the layer of photoaligning material to a light having a linear polarization and the light comprising a wavelength within the absorption band to convert the layer of photoaligning material into a layer of photoaligned material; applying a layer of a polymerizable liquid crystal over the layer of photoaligned material; performing photopoly- (Continued)

merization of the layer of polymerizable liquid crystal to form a liquid crystal polymer film; applying a solvent to the layer of photoaligned material, the solvent formulated to dissolve the photoaligned material to thereby release the liquid crystal polymer film from the support substrate; and removing the liquid crystal polymer film from the support substrate.

18 Claims, 11 Drawing Sheets

(51) Int. Cl.

| | | |
|---|---|---|
| *C07C 245/08* | (2006.01) | |
| *C09B 33/044* | (2006.01) | |
| *C09K 19/56* | (2006.01) | |
| *C09K 19/60* | (2006.01) | |

(52) U.S. Cl.
CPC ............ *C09K 19/56* (2013.01); *C09K 19/601* (2013.01); *G02F 1/133711* (2013.01); *G02F 1/133788* (2013.01); *C09K 2219/03* (2013.01)

(56) References Cited

U.S. PATENT DOCUMENTS

| | | | | |
|---|---|---|---|---|
| 4,983,332 | A * | 1/1991 | Hahn | B29C 33/62 264/1.1 |
| 5,989,758 | A * | 11/1999 | Komatsu | C08G 63/60 428/1.33 |
| 6,551,531 | B1 * | 4/2003 | Ford | B29D 11/00125 249/117 |
| 7,094,304 | B2 * | 8/2006 | Nystrom | B29D 11/00 156/242 |
| 8,520,170 | B2 * | 8/2013 | Escuti | G02B 5/3016 349/5 |
| 2002/0167639 | A1 * | 11/2002 | Coates | B29C 33/68 349/187 |
| 2003/0072896 | A1 * | 4/2003 | Kwok | C09B 35/14 428/1.23 |
| 2003/0152712 | A1 * | 8/2003 | Motomura | C09K 19/3852 427/402 |
| 2004/0105059 | A1 * | 6/2004 | Ohyama | G02F 1/133555 349/114 |
| 2006/0008649 | A1 * | 1/2006 | Shinichiro | B32B 7/06 428/411.1 |
| 2006/0222783 | A1 * | 10/2006 | Hayashi | C09K 19/3852 428/1.1 |
| 2007/0247586 | A1 * | 10/2007 | Tabirian | G02B 26/0825 349/200 |
| 2007/0258677 | A1 * | 11/2007 | Chigrinov | G02B 6/12007 385/15 |
| 2008/0278675 | A1 * | 11/2008 | Escuti | G02B 5/1833 349/201 |
| 2009/0256977 | A1 * | 10/2009 | Haddock | B29D 11/00028 349/13 |
| 2011/0097557 | A1 * | 4/2011 | May | C08J 7/047 428/195.1 |
| 2011/0188120 | A1 * | 8/2011 | Tabirian | G02B 27/44 359/573 |
| 2011/0234944 | A1 * | 9/2011 | Powers | C09K 19/544 349/86 |
| 2011/0262844 | A1 | 10/2011 | Tabirian et al. | |
| 2014/0055740 | A1 * | 2/2014 | Spaulding | G02C 7/04 351/159.02 |

OTHER PUBLICATIONS

Nersisyan et al. "Study of azo dye surface command photoalignment material for photonics applications", Appl. Opt., vol. 49(10), pp. 1720-1727 (Apr. 2010).*
Chigrinov et al. "Anchoring properties of photoaligned azo-dye materials" Phys. Rev., E vol. 68 061702 (Dec. 2003).*
Pagliusi et al. "Surface-induced photorefractivity in twistable nematics: toward the all-optical control of gain", Opt. Expr. vol. 16(21) pp. 16343-16351 (Oct. 2008).*
Nersisyan et al. "Characterization of optically imprinted polarization gratings", Appl. Opt., vol. 48(21) pp. 4062-4067 (Jul. 2009).*
Lee et al., "Generation of pretilt angles of liquid crystals on cinnamate-based photoalignment . . . ", Opt. Expr., vol. 17(26) pp. 23565-23575 (Dec. 2009).*
Yaroshchuk et al. "Azodyes as photoalignment agents for polymerizable liquid crystals", IDW'06 Digest vol. 1-3, pp. 83-86 (2006).*
Nersisyan et al. "Polarization insensitive imaging through polarization gratings", Opt. Expr. vol. 17(3) pp. 1817-1830 (Feb. 2009).*
N.V. Tabiryan, S.R. Nersisyan, D.M. Steeves and B.R. Kimball, "The Promise of Diffractive Waveplates", Optics and Photonics News, 21 (3), 41-45, 2010.
H. Sarkissian, B. Zeldovich, N. Tabiryan, "Longitudinally modulated bandgap nematic structure", JOSA B 23, 1712-1717, 2006.
U.S. Appl. No. 12/662,525, filed Apr. 2010, Tabirian et al.
H. Sarkissian, B.Y. Zeldovich and N.V. Tabiryan, "Polarization-universal bandgap in periodically twisted nematics", 1678 Optics Letters / vol. 31, No. 11 / Jun. 1, 2006.
N.V. Tabiryan, S.R. Nersisyan, D.M. Steeves and B.R. Kimball, The Promise of Diffractive Waveplates, 2010, Optics and Photonics News, 21 (3), 41-45.
S.R. Nersisyan, N.V. Tabiryan, D.M. Steeves, B.R. Kimball, V.G. Chigrinov, and H.-S. Kwok, Study of azo dye surface command photoalignment material for photonics applications, 2010, Appl. Opt. 49 (10), 1720-1727.
Sarik R. Nersisyan, Nelson V. Tabiryan, Diane M. Steeves, and Brian R. Kimball, Characterization of optically imprinted polarization gratings, 2009, Appl. Optics 48 (21), 4062-4067.
H. Sarkissian, B. Zeldovich, N. Tabiryan, "Longitudinally modulated bandgap nematic structure", 2006, JOSA B 23, 1712-1717.

* cited by examiner (a) (b)

METHOD OF FABRICATING A LIQUID CRYSTAL POLYMER FILM

CROSS REFERENCE TO RELATED APPLICATIONS

This application claims priority to U.S. Provisional Patent Application No. 61/775,899, filed Mar. 11, 2013, and which is hereby incorporated by reference.

STATEMENT REGARDING FEDERALLY SPONSORED RESEARCH OR DEVELOPMENT

This invention was made with Government support under Contract No. W911QY-12-C-0016.

RIGHTS OF THE GOVERNMENT

The invention described herein may be manufactured and used by or for the Government of the United States for all governmental purposes without the payment of any royalty.

TECHNICAL FIELD

The invention relates to a method of fabricating a liquid crystal polymer film. The field of applications of liquid crystal polymer films includes, for example, variable transmission lenses, flexible displays, laser beam steering and positioning systems, patterned phase-retardation films, diffractive waveplates, and polarization holograms.

BACKGROUND

Application of polymers in optical technologies is expanding due to low cost manufacturing, improved quality, and small weight. Polymers bring new qualities and opportunities in optical devices such as mechanical flexibility. Liquid crystal polymers, LCPs, have made it possible to inexpensively transform conventional liquid crystal displays, LCDs, into three-dimensional displays by application of half-wave phase retardation films with patterned optical axis orientation. Azobenzene polymer films have been used as optically deformable membrane mirrors.

Polymer optical components such as lenses are often fabricated by molding, and need to be released from the mold used for shaping them. Certain optical components such as phase retardation films and polarizers do not require molding into a complex shape, however they still need to be fabricated on a variety of substrates for mechanical stability and need releasing from their support substrates for transfer onto the devices and components they are designed for. A typical LCD, for example, comprises both a phase retardation film, for viewing angle enhancement, and polarizers, for contrast. Fabrication of polymer optical components in the form of coatings directly on the substrate they are intended for may be prohibited by technological and cost limitations.

The manufacturer of a final product often lacks the expertise, capability, resources and commercial incentives for expanding their manufacturing processes to all component materials. Just like computer manufacturers use processors and displays developed and produced by other companies, the LCD manufacturers use phase-retardation films and polarizers produced by specialized suppliers. Apart from those considerations, many of the substrates for polymer optics, such as those used for flexible displays, are not compatible with the organic solvents and processes used for their fabrication thus also requiring separate film fabrication, release and transfer techniques.

SUMMARY

The variety of materials and techniques developed for releasing polymer optics from their molds or substrates did not address the specifics and requirements of the class of polymer optics comprising liquid crystal polymers in the prior art, some examples of them are cited in the cross-references. LCPs are typically used for fabricating optical films with spatial modulation of optical axis orientation, such as vector vortex waveplates, cycloidal diffractive waveplates and polarization gratings, as discussed in N. V. Tabiryan, S. R. Nersisyan, D. M. Steeves and B. R. Kimball, "The Promise of Diffractive Waveplates", Optics and Photonics News, volume 21, number 3, pages 41-45, 2010. The orientation of molecules in LCPs is often coupled with the shape and form of the polymer film.

Thus, in the case of LCPs, substrates are can be needed not only for providing a form or support, but also for inducing the local orientation direction for the LCP molecules. This is achieved by coating the substrate, typically glass, with so-called alignment layer capable of producing anisotropic boundary conditions for the molecules of the polymerizable liquid crystal, LC.

The anisotropy axis that determines the orientation direction of LC molecules is typically created by mechanically buffing the alignment film. Buffing creates nano/micro-grooves in the alignment materials such as a polyimide. An alternative to mechanical buffing is the photoalignment technique, which offers the advantages of being a non-contact method, and allowing complex orientation patterns to be achieved. It is based on coatings that produce an anisotropy axis under the influence of a linear polarized light. Certain azobenzene dyes, including sulfonic bisazodyes are well suited for the photoalignment technique reported by S. R. Nersisyan, N. V. Tabiryan, D. M. Steeves, B. R. Kimball, V. G. Chigrinov, and H.-S. Kwok, "Study of azo dye surface command photoalignment material for photonics applications", Applied Optics, volume 49, number 10, pages 1720-1727, 2010. Due to absorption dichroism, highly efficient photoisomerization processes drive the azobenzene dyes to align perpendicular to the polarization direction of the light. Even a few nanometer thin films of thus photoaligned azobenzene dyes create anisotropic boundary conditions strong enough for alignment of LCP layers deposited on them.

Thus, the substrates used for fabrication of LCP optical structures, such as waveplates, and mirrors, etc., preferably should be able to carry an alignment layer that fulfilling one or more of the following: compatibility with the substrate, so that no deterioration of the optical qualities of the substrate occurs in the process of subjecting the substrate to the organic solvents used for coating the alignment material (this is a particular issue for flexible polymer substrates and polycarbonate); capability of producing a homogeneous thin film coating on a substrate; ability to provide adequate physical adhesion to the substrate; capability of creating anisotropic boundary conditions for a LC controlled by external influences; ability to exhibit strong orienting action on the LC; and the ability to withstand the fabrication process conditions of the LCP film and the component.

Naturally, the alignment materials that meet the requirements listed above are rather unique and have undergone decades of development. This is particularly true for photoalignment materials due to the complex processes involving their interaction both with light and with LCs. Incorporating a release film for LCPs may introduce a myriad of new variables in the fabrication process of LCP optics. To avoid it, in some cases, it was preferred to fabricate the LCP using known materials and processes and then dissolve the substrates in hazardous solvents rather than to try adapting a release film to the process. Mechanical stresses applied when separating LCP films from substrates without proper release layers affect their optical quality and the optical modulation patterns, and compromise the mechanical integrity of the LCP films, that, for example, are only a few micrometer thick in case of waveplates.

It is an object of the present invention to provide an improved method of fabricating a liquid crystal polymer film. It is a further object of the present invention to provide an improved liquid crystal polymer release material.

A first aspect of the invention provides a method of fabricating a liquid crystal polymer film. The method comprises steps (a) to (g). Step (a) comprises providing a support substrate having a surface having a shape arranged to define a form of a liquid crystal polymer film to be fabricated. Step (b) comprises applying a layer of a photoaligning material over said surface of said support substrate. Said photoaligning material has an absorption band. Step (c) comprises exposing said layer of photoaligning material to a light having a linear polarization and said light comprising a wavelength within said absorption band. Exposing said layer of photoaligning material to the light converts the layer of photoaligning material into a layer of photoaligned material. Step (d) comprises applying a layer of a polymerizable liquid crystal over said layer of photoaligned material. Step (e) comprises performing photopolymerization of said layer of polymerizable liquid crystal to form a liquid crystal polymer film. Step (f) comprises applying a solvent to said layer of photoaligned material. Said solvent is formulated to dissolve said photoaligned material, to thereby release said liquid crystal polymer film from said support substrate. Step (g) comprises removing said liquid crystal polymer film from said support substrate.

The photoaligned material layer may both perform alignment of the polymerisable liquid crystal and act as a release layer for the liquid crystal polymer, LCP, film from the substrate. The method may thus enable fabrication of a LCP film using materials that combine photoalignment capability with LCP release function. The method may enable non-contact release of LCPs from substrates without affecting their optical quality and alignment properties. The method may enable LCPs to be released from a support substrate while maintaining their mechanical and optical characteristics and without a direct physical influence or a mechanical stress. The method may enable the release of LCPs onto substrates made of materials that are not suitable for direct fabrication of LCP optical components due to poor chemical resistivity to solvents involved in the process and/or poor mechanical strength. The method may enable LCP films to be provided on substrates of complex shape, such as lenses.

In an embodiment, said photoaligning material has a molecular structure comprising at least one photoresponsive compound. The photoresponsive compound may ensure that the photoaligning material is able to provide photoalignment for liquid crystal molecules including monomers.

In an embodiment, said at least one photoresponsive compound is one of azobenzene, stilbene, azoxy, azomethine, fulgide and diarylethene. Use of the identified photoresponsive compounds may ensure that the photoaligning material is able to provide photoalignment for liquid crystal molecules including monomers.

In an embodiment, said solvent is a polar solvent and said photoaligning material has a molecular structure comprising at least one functional group for solubility in a polar solvent. In an embodiment, said solvent is one of water, Dimethylformamide, and a low molecular weight alcohol.

In an embodiment, said at least one functional group is a sulfo group. This may provide adhesion of the photoaligning material to the support substrate.

In an embodiment, said support substrate is chemically resistant to said solvent. This may ensure that the support substrate does not deteriorate during the fabrication of the LCP film.

In an embodiment, the method comprises, before exposing said layer of photoaligning material to said light, spatially modulating said linear polarization of said light. This may enable complex alignment patterns, and thus complex orientation patterns in the LCP film, to be produced.

In an embodiment, said linear polarization of said light is spatially modulated by transmitting said light through a spatial light polarization modulator. This may enable complex alignment patterns, and thus complex orientation patterns in the LCP film, to be produced.

In an embodiment, said spatial light polarization modulator is configured to apply one of a one-dimensional polarization pattern and a two-dimensional polarization pattern.

In an embodiment, said linear polarization of said light is spatially modulated with one of a one-dimensional polarization pattern and a two-dimensional polarization pattern.

In an embodiment, said linear polarization of said light is spatially modulated by transmitting said light through one of a cycloidal diffractive waveplate, a vector vortex waveplate, and an array of vector vortex waveplates. This may enable complex alignment patterns, and thus complex orientation patterns in the LCP film, to be produced.

In an embodiment, said photoaligned material is insoluble in at least one of hexanes, cyclohexane, ketones such as cyclopenthanone, and esthers such as Propylene glycol monomethyl ether acetate, PGMEA. The photoaligned material is therefore insoluble in many organic solvents often used for polymerizable liquid crystals.

In an embodiment, after step (e) the method comprises attaching said liquid crystal polymer film to a carrier substrate. Step (g) comprises removing said liquid crystal polymer film on said carrier substrate from said support substrate. The method may enable the LCP film to be fabricated on one substrate, typically made of mechanically strong and chemically resistant materials, onto a substrate which may be difficult to handle or otherwise not compatible with the LCP fabrication process due to wettability, temperature, solvents, or a complex shape and surface topology.

In an embodiment, said liquid crystal polymer film is attached to said carrier substrate by applying a layer of an adhesive onto said liquid crystal polymer film and performing photopolymerization of said layer of said adhesive to form said carrier substrate. This may enable the LCP film to be attached to a carrier substrate without any mechanical stress being applied to the LCP film, which may reduce risk of damage to the LCP film during the attachment process.

In an embodiment, said carrier substrate is a polymer film which is thicker and stronger than said liquid crystal polymer film. Such a carrier substrate may act as a support backbone for the LCP film.

In an embodiment, said liquid crystal polymer film is attached to said carrier substrate by applying a layer of an adhesive onto said carrier substrate, and then bringing said support substrate and said carrier substrate together to bring said adhesive into contact with said liquid crystal polymer film. Said adhesive is then cured. This may enable the LCP film to be attached to a more substantial carrier substrate still without any mechanical stress being applied to the LCP film, which may reduce risk of damage to the LCP film during the attachment process.

In an embodiment, after step (e) the method comprises adhering the liquid crystal polymer film to a second support substrate. The method further comprises performing additional steps a. and b. after step (g). Step a. comprises providing a third support substrate carrying a second layer of a photoaligned material. The third support substrate has a second liquid crystal polymer film, different to the first liquid crystal polymer film, provided over said second layer of a photoaligned material. Step b. comprises applying a solvent to said second layer of a photoaligned material. Said solvent is formulated to dissolve said photoaligned material to thereby release said second liquid crystal polymer film from said third support substrate. A support substrate carrying two overlaid LCP films may therefore be formed, which may enable a composite LCP film having a varying or more complex orientation pattern to be formed.

In an embodiment, said first liquid crystal polymer film has a first alignment pattern and said second liquid crystal polymer film has a second alignment pattern. Said second alignment pattern is one of a different pattern to the first alignment pattern and a different orientation to said first alignment pattern. A support substrate carrying two overlaid LCP films may therefore be formed, which may enable a composite LCP film having a varying or more complex orientation pattern to be formed. A composite LCP film may be formed in this way in which the two alignment patterns have mutually perpendicular orientation patterns, to thereby produce a photonic bandgap structure described in H. Sarkissian, B. Zeldovich, N. Tabiryan, "Longitudinally modulated bandgap nematic structure", JOSA B 23, 1712-1717, 2006.

In an embodiment, said support substrate is a first mold segment and step (a) further comprises providing a second mold segment. The second mold segment has a surface which has a shape arranged to cooperate with said surface of said first mold segment. Said surfaces of said first and second mold segments together define a cavity which defines said shape of said liquid crystal polymer film to be fabricated. Step (d) comprises arranging said first and second mold segments together to form said cavity and then filling said cavity with said polymerizable liquid crystal. This may enable LCP films having a complex, non-planar shapes, such as a spherical lens, to be formed.

In an embodiment, step (b) further comprises applying a layer of said photoaligning material over said surface of said second mold segment. Step (c) comprises exposing both said layers of photoaligning material to a light having a linear polarization and said light comprising a wavelength within said absorption band to convert each said layer of photoaligning material into a layer of photoaligned material.

In an embodiment, step (b) further comprises applying a layer of said photoaligning material over said surface of said second mold segment. Step (c) comprises exposing said layer of photoaligning material on said first mold segment to a first linearly polarized light having a first polarization spatial modulation. Step (c) additionally comprises exposing said layer of photoaligning material on said second mold segment to a second linearly polarized light having a second polarization spatial modulation, different to said first polarization spatial modulation. Each said linearly polarized light comprises a wavelength within said absorption band to convert each said layer of photoaligning material into a respective layer of photoaligned material.

In an embodiment, said absorption band comprises a wavelength in the ultra-violet, UV, or visible part of the optical spectrum.

In an embodiment, step (c) comprises providing an exposure dose of said light in dependence on at least one of a characteristic of said photoaligning material and a wavelength of said light.

In an embodiment, step (b) comprises applying said photoaligning material over said surface of said support substrate by one of dip coating, printing, stamping and spin coating. This may ensure that the resulting photoalignment layer has a thickness capable of being effectively dissolved in said solvent, particularly water.

In an embodiment, step (d) comprises applying said layer of said polymerizable liquid crystal by spin coating.

In an embodiment, said polymerizable liquid crystal comprises functional groups, copolymers and additives to control its optical, electro-optical, mechanical, thermodynamic, and chemical properties.

A second aspect of the invention provides a liquid crystal polymer release material comprising a first functional group, a second functional group and a third functional group. The first functional group is characterised for photoalignment of liquid crystal materials. The second functional group is characterised for solubility in a polar solvent. The third functional group is characterised for adhesion to a substrate material.

The LCP release material may perform alignment of the polymerisable liquid crystal and act as a release layer for the liquid crystal polymer, LCP, from, for example, a substrate. The LCP release material may enable non-contact release of LCPs from substrates without affecting their optical quality and alignment properties. The LCP release material may enable LCPs to be released from a support substrate while maintaining their mechanical and optical characteristics and without a direct physical influence or a mechanical stress. The LCP release material combines LCP alignment capabilities, in particular capability for photoalignment, with a release function. The LCP release material may enable the release of LCPs onto substrates made of materials that are not suitable for direct fabrication of LCP optical components due to poor chemical resistivity to solvents involved in the process and/or poor mechanical strength. The LCP release material may enable LCP films to be provided on substrates of complex shape, such as lenses.

In an embodiment, said first functional group is a photoresponsive compound. The photoresponsive compound may ensure that the photoaligning material is able to provide photoalignment for liquid crystal molecules including monomers.

In an embodiment, said first functional group is one of Azobenzene, Stilbene, Azoxy, Azomethine, Fulgide and Diarylethene. The photoresponsive compound may ensure that the photoaligning material is able to provide photoalignment for liquid crystal molecules including monomers.

In an embodiment, said second functional group is a sulfo group. This may provide adhesion of the photoaligning material to the substrate material.

In an embodiment, second functional group is characterised for solubility in one of water, Dimethylformamide, and a low molecular weight alcohol. The photoresponsive compound may ensure that the photoaligning material is able to provide photoalignment for liquid crystal molecules including monomers.

In an embodiment, said substrate material is an optical substrate.

In an embodiment, said substrate material is one of glass, polycarbonate, fused silica, Zinc selenide, ZnSe, and Barium fluoride, BaF2.

A third aspect of the invention provides a method for preparing a liquid crystal polymer film comprising the steps of:
- (a) providing a substrate;
- (b) dispensing a photoaligning release material layer over said substrate;
- (c) exposing said photoaligning release material layer to a linear polarized light;
- (d) dispensing a polymerizable liquid crystal over the photoaligned release material layer;
- (e) in-situ reacting said polymerizable liquid crystal to form a polymer film;
- (f) immersing said substrate comprising said photoaligned release material layer and said polymerized liquid crystal layer into a solvent, said solvent capable of dissolving said photoaligned release material layer;
- (g) separating the polymerized liquid crystal film from the substrate.

In an embodiment, the molecular structure of said photoaligning release material comprises at least one photoresponsive core such as azobenzene, stilbene, azoxy, azomethine, fulgide and diarylethene.

In an embodiment, the molecular structure of said photoaligning release material comprises special groups for water solubility such as sulfo groups.

In an embodiment, linear polarization of said polarized light is modulated by a spatial light polarization converter.

In an embodiment, said spatial light polarization converter is a cycloidal diffractive waveplate, vector vortex waveplate, arrays of vector vortex waveplates, or other 1- or 2-D polarization patterns.

In an embodiment, said solvent is a polar like water, DMF, or a low molecular weight alcohol A fourth aspect of the invention provides a method for preparing a liquid crystal polymer film comprising the steps of:
- (a) providing a mold, including at least two cooperating mold segments, having a cavity therein for forming the molded liquid crystal polymer film;
- (b) dispensing a photoaligning release material layer over the surfaces of at least one of the segments of the mold;
- (c) exposing the photoaligning release material layers at least on one of the segments of the mold to a linear polarized light that is, generally, spatially modulated and different for each segment of the mold;
- (d) closing the mold;
- (e) injecting liquid crystal polymeric precursor materials into the mold cavity;
- (f) reacting in situ the liquid crystal polymeric precursor materials to form the molded polymer;
- (g) immersing the mold into a solvent, said solvent capable of dissolving said photoaligned release material layers;
- (h) parting at least one of the mold sections.

In an embodiment, said polymerizable liquid crystal contains functional groups, copolymers and additives to control its optical, electro-optical, mechanical, thermodynamic, and chemical properties.

A fifth aspect of the invention provides a method for preparing a liquid crystal polymer film comprising the steps of:
- (a) providing a mold comprising the first and the second segments that are congruent at least in part;
- (b) dispensing a photoaligning release material layer over the surface of the first segment of the mold;
- (c) exposing said photoaligning release material layer to a pattern of linear polarized light;
- (d) dispensing a polymerizable liquid crystal precursor over the photoaligned release material layer;
- (e) in-situ reacting said polymerizable liquid crystal to form a polymer film;
- (f) dispensing an adhesive layer over the second segment of the mold;
- (g) closing the mold;
- (h) curing the adhesive;
- (f) immersing the mold into a solvent, said solvent capable of dissolving said photoaligned release material layer;
- (g) parting the first segment of the mold.

In an embodiment, said polymerizable liquid crystal contains functional groups, copolymers and additives to control its optical, electro-optical, mechanical, thermodynamic, and chemical properties.

A sixth aspect of the invention provides a mold release material comprising at functional groups in their molecular structure, said functional groups providing:
- (a) photoalignment for liquid crystalline materials;
- (b) solubility in polar solvents like water, DMF, and low molecular weight alcohols;
- (c) adhesion to a substrate made of a material selected from the group consisting of glass, polycarbonate, fused silica, ZnSe, BaF2, and other materials commonly used in optics, including infra-red, IR, and Terahertz, THz, optics.

Several aspects of the invention are described above, in varying detail as to the features of each of the aspects. Any of the features of one of the aspects can be included as an additional or alternative feature of any of the other aspects, practices or embodiments of the disclosure described herein, except where clearly mutually exclusive with another feature of an aspect, practice or embodiment or where a statement is explicitly made herein that certain features will not work in such a combination. To avoid undue repetition and length of the disclosure, every possible combination is not explicitly recited. Furthermore, as the skilled worker can ascertain, a method of the present disclosure can comprise the steps relating to the function or operation of the features of apparatus and systems disclosed herein.

DETAILED DESCRIPTION

Before explaining the disclosed embodiment of the present invention in detail it is to be understood that the invention is not limited in its application to the details of the particular arrangement shown since the invention is capable of other embodiments. Also, the terminology used herein is for the purpose of description and not limitation.

Figure 1:
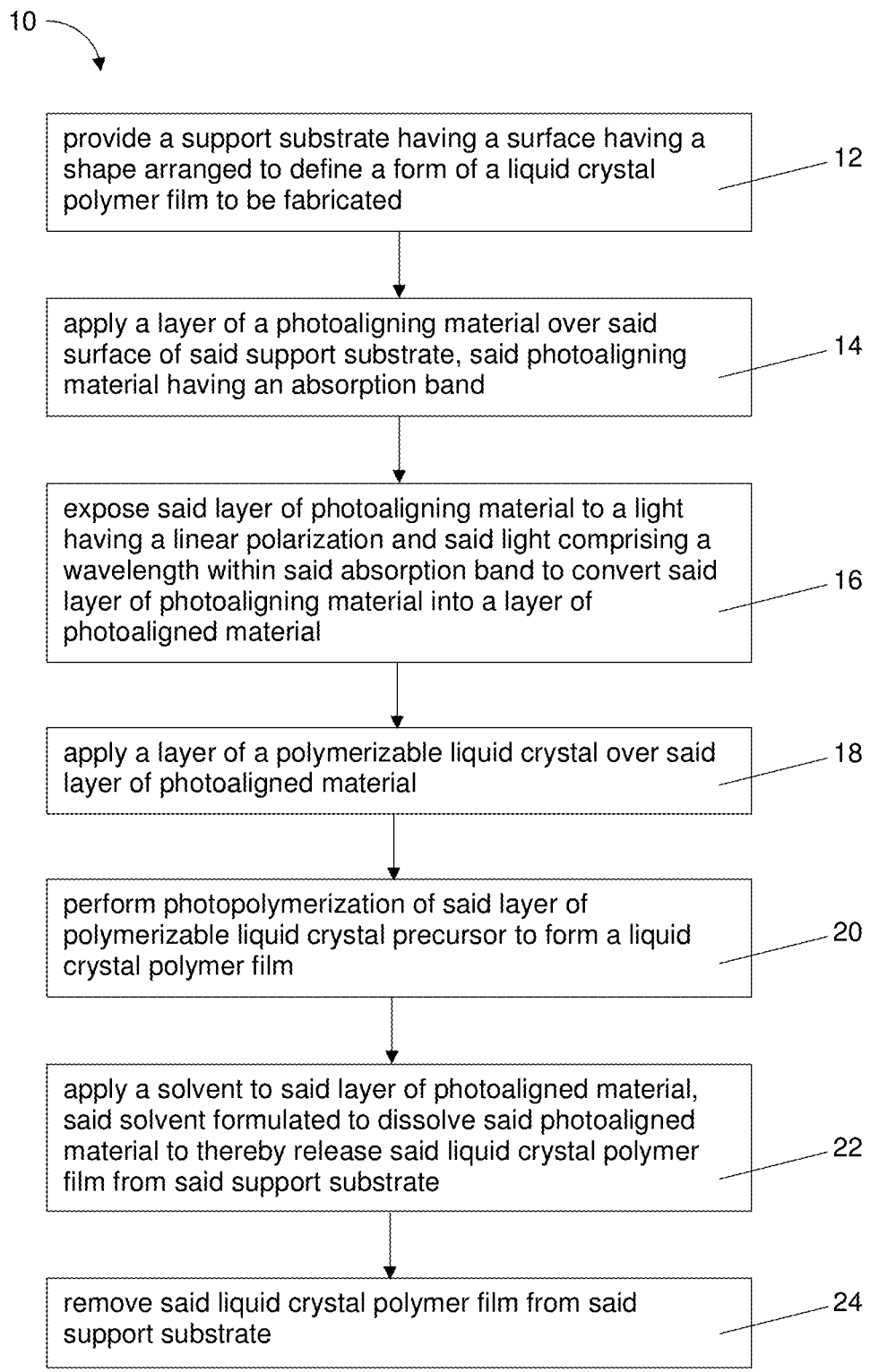
FIG. 1 shows the steps of a method according to a first embodiment of the invention of fabricating a liquid crystal polymer film.

Referring to FIG. 1, a first preferred embodiment of the invention provides a method 10 of fabricating a liquid crystal polymer film 121.

The method comprises steps (a) to (g), as follows. In step (a) 12 a support substrate is provided. The support substrate has a surface which has a shape arranged to define a form of the liquid crystal polymer, LCP, film that is to be fabricated. In step (b) 14 a layer of a photoaligning material is applied over the surface of the support substrate. The photoaligning material has an absorption band. In step (c) 16 the said layer of photoaligning material is exposed to a light having a linear polarization to convert the layer of photoaligning material into a layer of photoaligned material. The light comprises a wavelength within the absorption band of the photoaligning material.

In step (d) 18 of the method, a layer of a polymerizable liquid crystal is applied over the layer of photoaligned material 111. In step (e) 20 photopolymerization of the layer of polymerizable liquid crystal is performed, to form a liquid crystal polymer, LCP, film.

Step (f) 22 comprises releasing the liquid crystal polymer film from the support substrate by applying a solvent to the layer of photoaligned material. The solvent is formulated to dissolve the photoaligned material, to thereby release the LCP film. In the final step (g) 24, the liquid crystal polymer film is removed from the support substrate.

Figure 2:
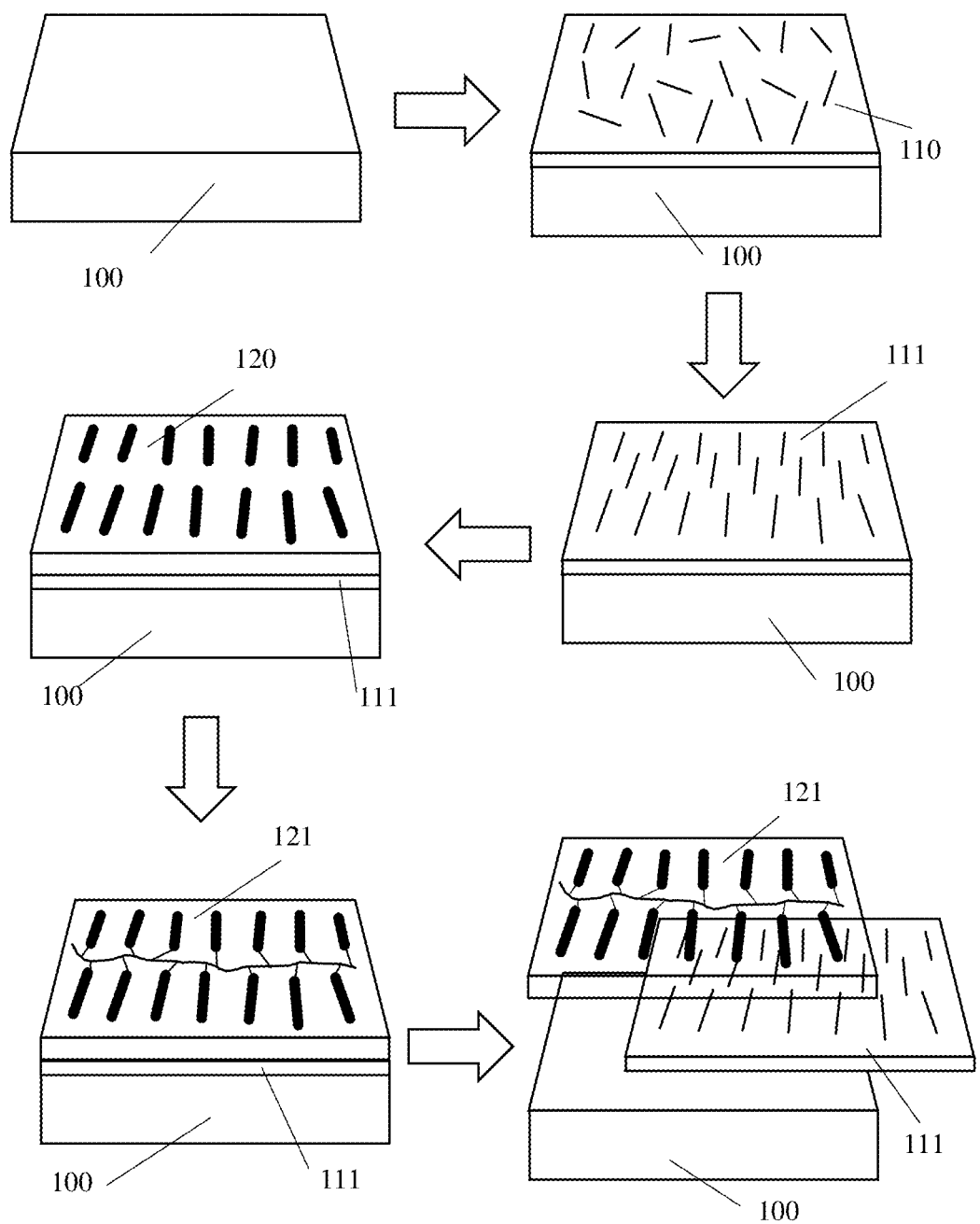
FIG. 2 schematically shows a method according to a second embodiment of the invention of fabricating a liquid crystal polymer film.

In a second embodiment, illustrated in FIG. 2, the invention provides a method of fabricating a liquid crystal polymer film 121. The method of this embodiment is similar to the method 10 of the first embodiment, with the following modifications.

In this embodiment, the photoaligning material comprises an azobenzene dye based on chromocentranine R structures which comprise a sulfo group. An example of such a dye is sulfonic bisazodye SD1:

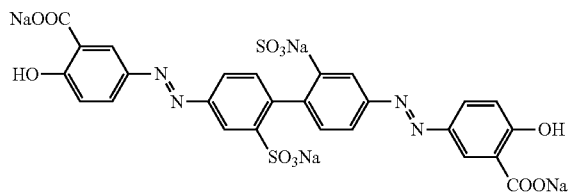

Such materials meet the key conditions required for the preferred embodiment of the current invention: 1) solubility in water and other polar (hydrophilic) solvents such as DMF and low molecular weight alcohols; 2) insolubility in organic solvents often used for polymerizable liquid crystals, among them, hexanes, cyclohexane, ketones like cyclopenthanone, esthers like PGMEA, etc.; and 3) capability of providing photoalignment for liquid crystal molecules, including, monomers due to the presence of azobenzene group in their molecular structure. Other photoresponsive cores such as azoxy, azomethine, fulgide and diarylethene, could be used as well.

Typically, azobenzene dyes meeting all the conditions above are in the form of a powder at room temperature, and they can be used for coating by dissolving them in a variety of solvents, including water. The concentration of the azo dye in the solvent determines film thickness and the coating technique. Variety of coating techniques are applicable, including dip coating, printing, stamping, and spin coating. In the latter case, approximately 1 wt. % of said azo dye can be used in a DMF as solvent. Spinning at 3000 rpm for 60 s provides thus a photoalignment layer of a few tens of nm thickness capable of being effectively dissolved in water.

The photoalignment film 110 is coated on a substrate 100 that is chemically resistive to the solvents used in the process, glass, for example. The photoalignment film 110 is exposed to polarized light comprising a wavelength in the absorption band of the photoalignment material. The absorption band can be in the UV or visible part of the spectrum. The light is generally polarized by a polarizer and a spatial light polarization modulator. The exposure dose depends on the specific photoalignment material and the radiation wavelength. For example, PAAD-72 azobenzene (available at www.beamco.com), for example, produces high quality alignment conditions for common liquid crystals such as 4-pentyl-4'-cyanobiphenyl (5CB) as well as for Merck's RMS series reactive mesogens within a 5 minute exposure time to a UV radiation of 325 nm wavelength and 10 mW/cm2 power density.

The substrate coated by the photoaligned azobenzene dye layer 111 is further coated with a polymerizable liquid crystal, LC 120. For example, an RMS series LC material available from Merck can be used and may be applied on the photoalignment layer 111 by spin coating. The spinning regime is chosen from considerations of required film thickness or phase retardation. As an example, an approximately half-wavelength phase retardation for a light beam of 400 nm wavelength is obtained by spin coating at 3000 rpm for 60 s. The polymerizable liquid crystal layer 120 thus aligned can be crosslinked by photopolymerization with an unpolarized UV light.

The crosslinked polymer film 121 thus obtained is released from the substrate 100 by submerging the substrate in water, which causes dissolution of the azobenzene dye layer. The release takes place within minutes affecting neither the alignment conditions nor the mechanical properties of the crosslinked polymer film 121.

Figure 3:
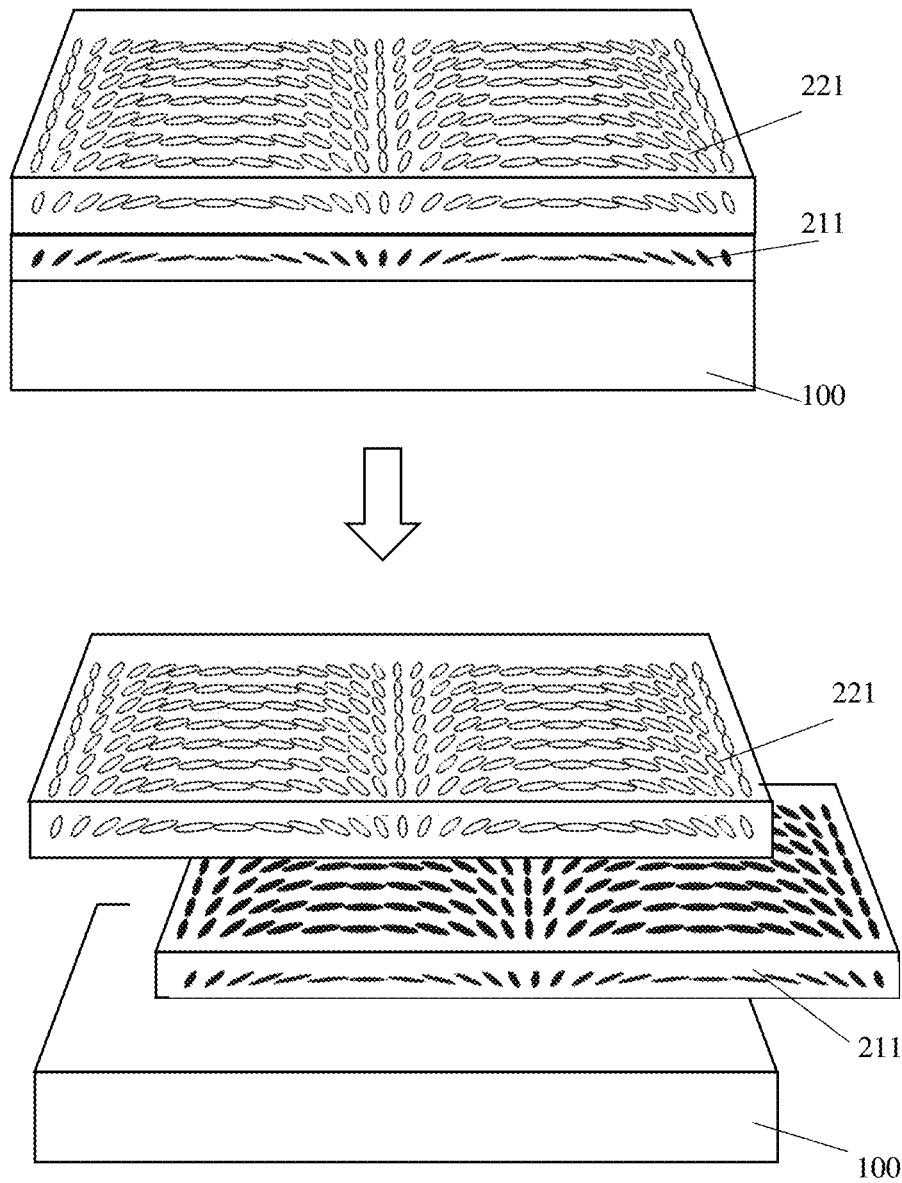
FIG. 3 schematically shows a method according to a third embodiment of the invention of fabricating a liquid crystal polymer film.

In a third embodiment, illustrated in FIG. 3, the invention provides a method of fabricating a liquid crystal polymer film 221. The method of this embodiment is similar to the previous embodiments, with the following modifications.

In this embodiment, the layer photoaligning material is exposed to light having a spatially modulated linear polarization. The method comprises, before exposing the layer of photoaligning material to the light, spatially modulating the linear polarization of the light.

The linear polarization of the light may be spatially modulated with either a one-dimensional polarization pattern or a two-dimensional polarization pattern. In this example, the linear polarization of the light is spatially modulated by transmitting the light through a cycloidal diffractive waveplate. The light may alternatively be transmitted through a vector vortex waveplate or an array of vector vortex waveplates.

In contrast to the homogeneous alignment of the LCP molecules shown in FIG. 2, spatially modulating the polarization of the light used to expose the photoaligning material enables one to produce more complex orientation patterns. For example, using diffractive waveplates as linear-to-radial or linear-to-cycloidal polarization converters, as disclosed in U.S. patent application Ser. No. 12/662,525, and described in Sarik R. Nersisyan, Nelson V. Tabiryan, Diane M. Steeves, and Brian R. Kimball, "Characterization of optically imprinted polarization gratings", Applied Optics, volume 48, number 21, pages 4062-4067, 2009, the method of this embodiment may be used to fabricate a diffractive waveplate LCP films. FIG. 3 shows a substrate 100 on which a cycloidal aligned photoalignment-release layer coating 211 is provided and a cycloidal aligned crosslinked liquid crystal polymer 221. A cycloidal diffractive waveplate LCP film is released in this case.

Figure 4:
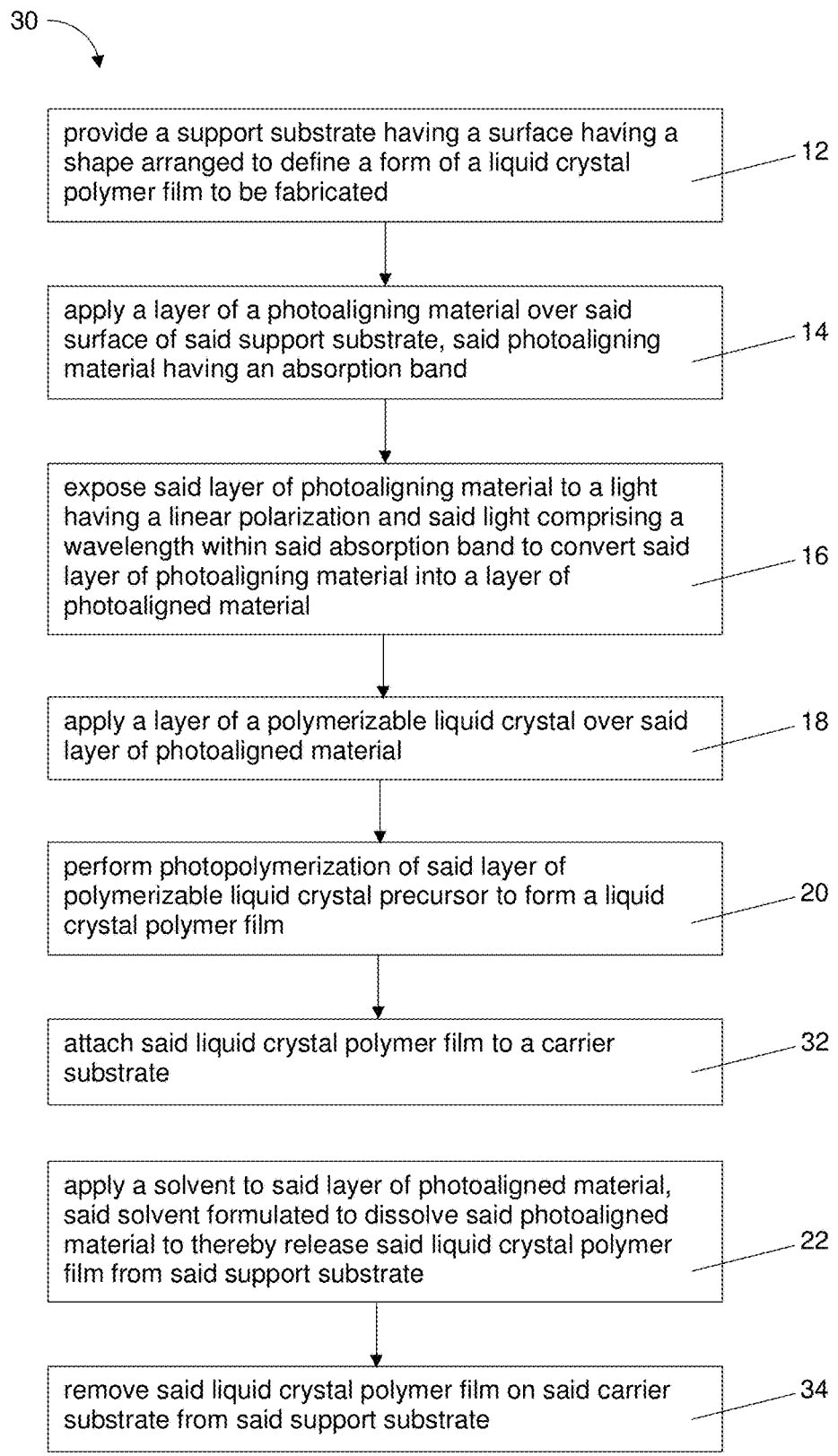
FIG. 4 shows the steps of a method according to a fourth embodiment of the invention of fabricating a liquid crystal polymer film.

In a fourth embodiment, illustrated in FIG. 4, the invention provides a method 30 of fabricating a liquid crystal polymer film 121. The method 30 of this embodiment is similar to the method 10 of the first embodiment, with the following modifications. The same reference numbers are retained for corresponding steps.

In this embodiment, after step (e) the method 30 comprises attaching said liquid crystal polymer film to a carrier substrate 32. Step (g) comprises removing said liquid crystal polymer film on said carrier substrate from said support substrate 34.

Figure 5:
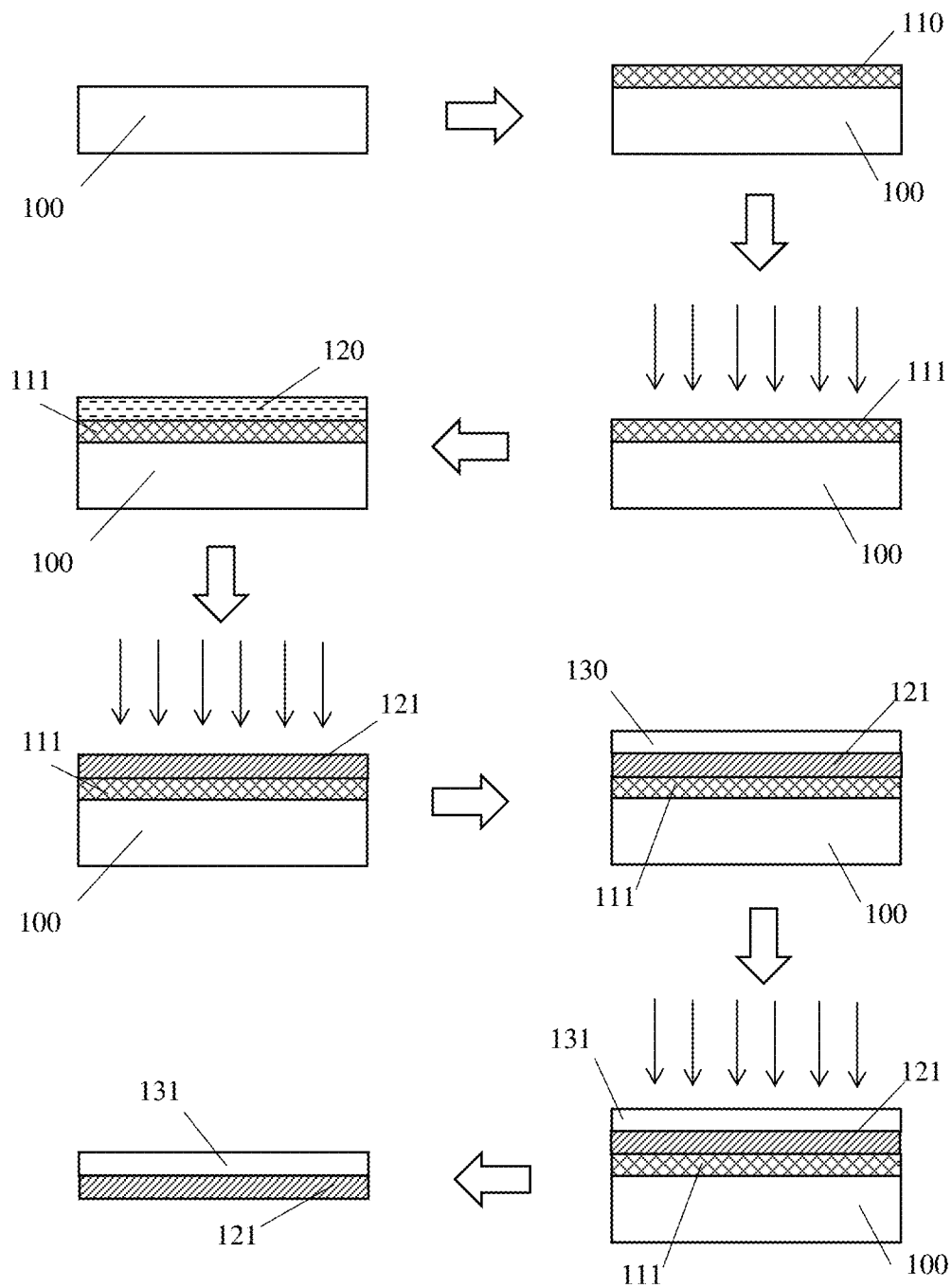
FIG. 5 schematically shows a method according to a fifth embodiment of the invention of fabricating a liquid crystal polymer film.
Figure 6:
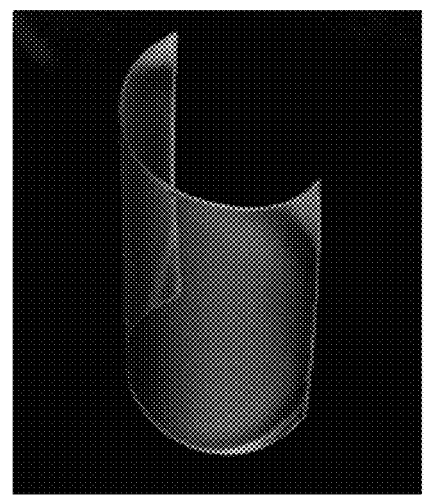
FIG. 6 shows a photo of a homogeneously aligned LCP film transferred onto a flexible polymer support film.
Figure 7:
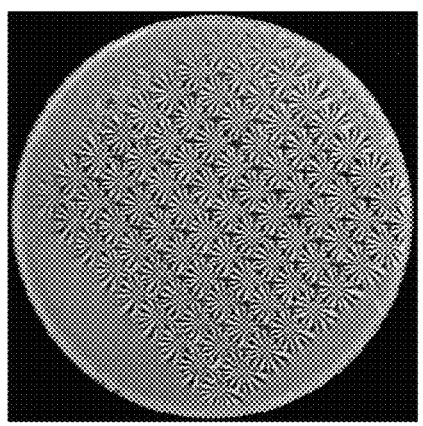
FIG. 7 shows (a) a photo of a LCP film with an array of axially modulated optical axis orientation fabricated on a fused silica substrate and (b) a photo of the LCP film transferred onto a polycarbonate substrate.
Figure 7:
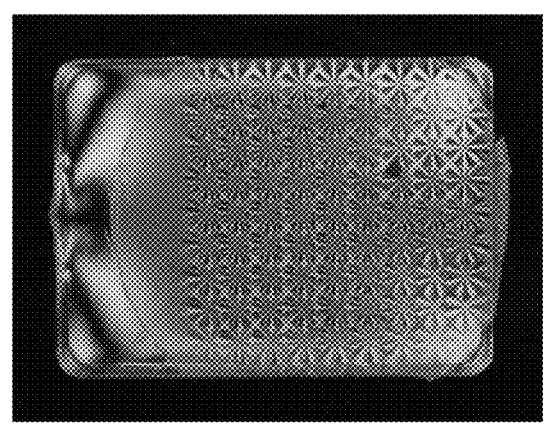

In a fifth embodiment, illustrated in FIGS. 5 to 7, the invention provides a method of fabricating a liquid crystal polymer film 121. The method of this embodiment is similar to the method of the second embodiment, with the following modifications.

The opportunity of releasing LOP films produced on substrates coated with photoaligning release layers can be used for transferring the films produced on a given substrate, typically made of mechanically strong and chemically resistant materials, onto substrates that are either difficult to handle or otherwise are not compatible with LCP fabrication processes due to wettability, temperature, solvents, or complex shape and surface topology.

In this embodiment, the LCP film 121 is transferred to another polymer film 131 that may generally be thicker and stronger mechanically to act as a support backbone for the LCP film 121. The method of this embodiment is the same as the method illustrated in FIG. 2, up to the stage of obtaining the crosslinked optical polymer film 121. In this embodiment, an optical adhesive 130, for example NOA-68 (available from Norland), is coated on top of the crosslinked optical film 121 by spin coating at 4000 rpm for 60 s. The layer of optical adhesive 130 is then exposed to a UV light of 365 nm wavelength for 10 minutes to cause photopolymerization of the optical adhesive 130, to thereby form the support film 131. The support substrate 100, photoalignment layer 111, LCP film 121 and support film 131 are then submersed in water, which results in releasing the optical film 121, carried by the support film 131, from the support substrate 100.

FIG. 6 shows an example of an anisotropic optical film of approximately 1 μm (micrometer) thickness attached to a thick polymer backing and FIGS. 7a and 7b show the transfer of an LCP film 421 in the form of an array of vector vortex waveplates produced on a fused silica substrate onto a polycarbonate support film 422.

Figure 8:
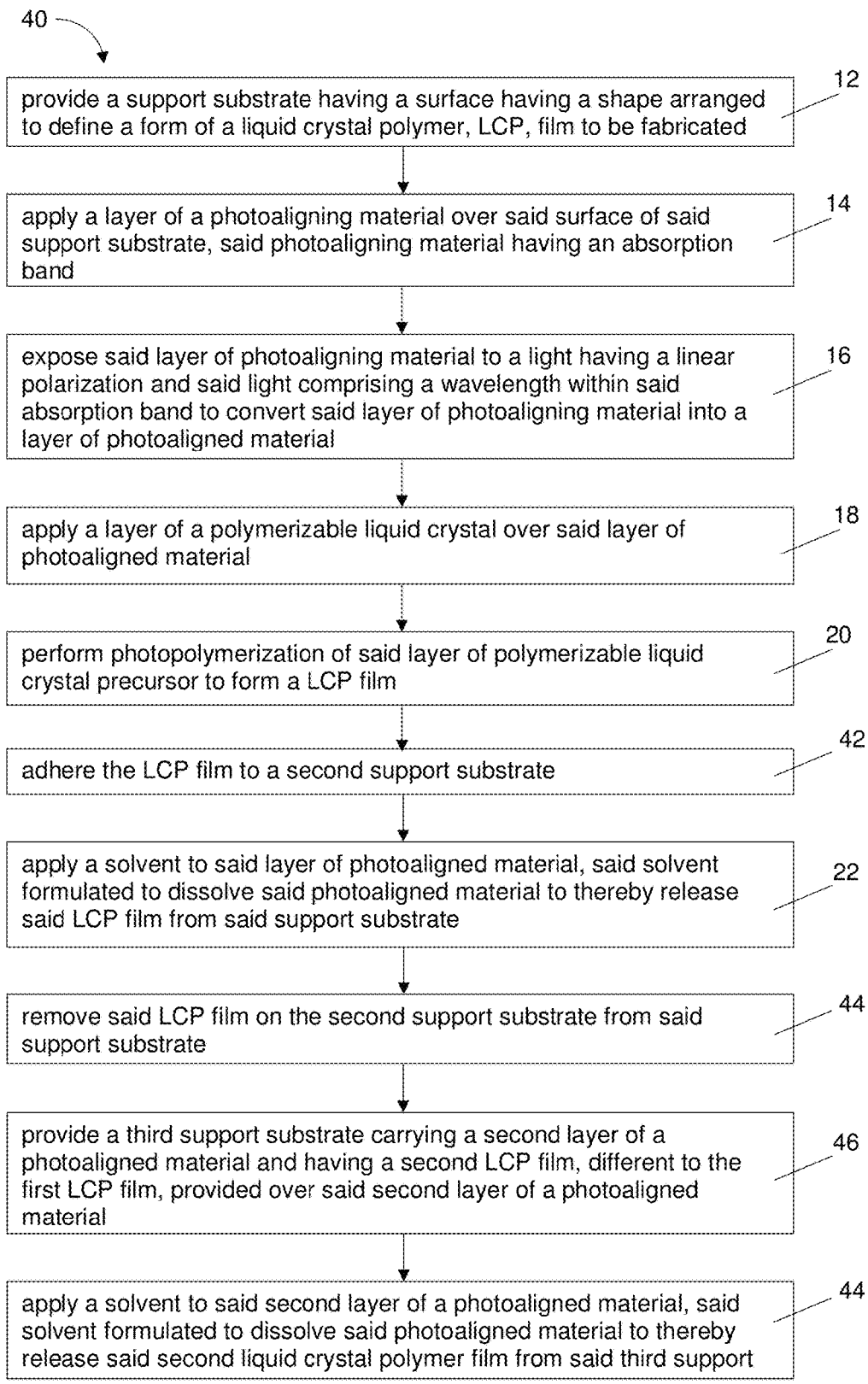
FIG. 8 shows the steps of a method according to a sixth embodiment of the invention of fabricating a liquid crystal polymer film.

In a sixth embodiment, illustrated in FIG. 8, the invention provides a method 40 of fabricating a liquid crystal polymer film which is similar to the method 10 of the first embodiment, with the following modifications.

In this embodiment, after step (e) the method 40 comprises, after step (e), the step of adhering the liquid crystal polymer film to a second support substrate 42. Solvent is then applied to the layer of photoaligned material, to dissolve the photoaligned material and release the LCP film from the support substrate 22 and the LCP film attached to the second support substrate is removed from the support substrate on which it was formed.

The method further comprises, after step (g), providing a third support substrate carrying a second layer of a photoaligned material 46. The third support substrate has a second liquid crystal polymer film, different to the first liquid crystal polymer film, provided over the second layer of a photoaligned material. A solvent is then applied to the second layer of a photoaligned material. The solvent is formulated to dissolve the photoaligned material to thereby release the second LCP film from the third support substrate. The two LCP films are thereby left on the second support substrate.

Figure 9:
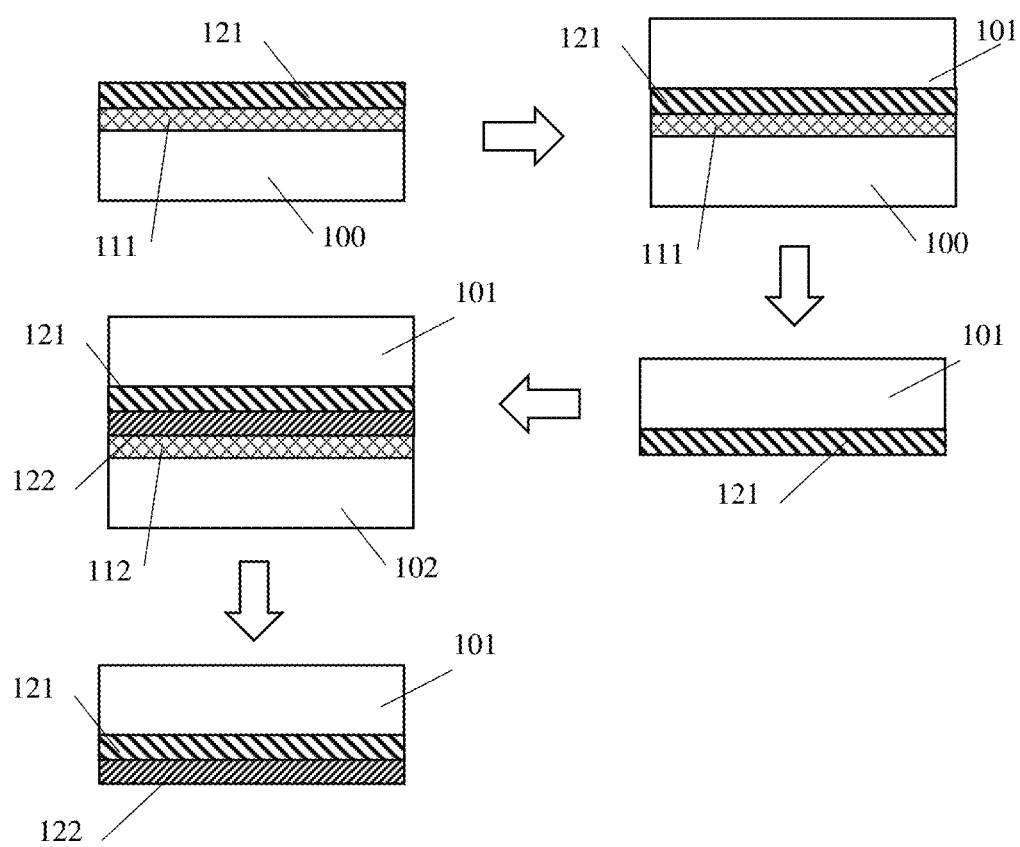
FIG. 9 schematically shows a method according to a seventh embodiment of the invention of fabricating a liquid crystal polymer film.

Referring to FIG. 9, a seventh embodiment of the invention provides a method of fabricating a liquid crystal polymer film which is similar to the method of the illustrated in FIG. 2, with the following modifications. The same reference numbers are retained for corresponding features.

In this embodiment, a first LCP film 121 is transferred onto a second LCP film 122, as follows. The substrate 100 carrying the photoalignment layer 111 and the crosslinked LCP film 121 with optical axis aligned according to the photoalignment pattern produced on said photoalignment layer 111 is attached to a second support substrate 101 by an adhesive layer (not shown). Submersion in water then releases the original support substrate 100 by dissolving the photoalignment layer 111. The LCP film 121, carried by the second support substrate 101, is then attached to a second LCP film 122 of generally different pattern or different orientation. The second LCP film 122 is carried on a third support substrate 102 via a further photoalignment layer 112.

The third support substrate 102 is then released by dissolving the further photoalignment layer 112, resulting in the second support substrate 101 carrying both of the LCP films 121, 122. As an example, the two LCP films could be homogeneously aligned LCP films having a mutually perpendicular orientation of their optical axes, to produce a photonic bandgap structure such as the one described in H. Sarkissian, B. Zeldovich, N. Tabiryan, "Longitudinally modulated bandgap nematic structure", Journal of the Optical Society of America B, volume 23, pages 1712-1717, 2006.

Figure 10:
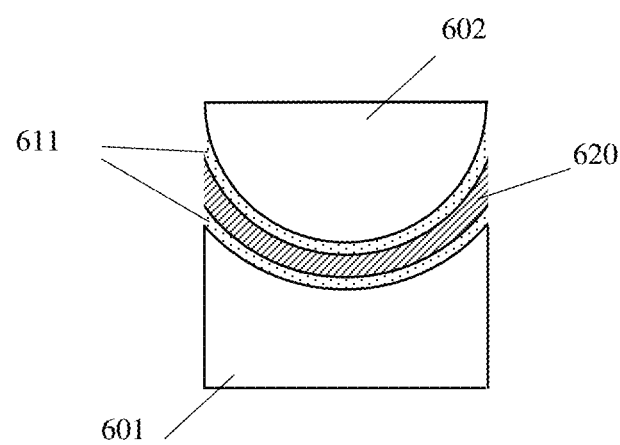
FIG. 10 schematically shows a method according to an eighth embodiment of the invention of fabricating a liquid crystal polymer film.

FIG. 10 illustrates a method according to an eighth embodiment of the invention of fabricating a liquid crystal polymer film. The method of this embodiment is similar to the method 10 of the first embodiment, with the following modifications.

In this embodiment, the support substrate is a first mold segment 601 and step (a) further comprises providing a second mold segment 602 which has a surface having a shape arranged to cooperate with the surface of the first mold segment 601. The surfaces of the first and second mold segments together define a cavity which defines the shape with which the LCP film 620 is to be fabricated. Step (b) further comprises applying a layer of the photoaligning material over the surface of the second mold segment 602 and in step (c) the layer of photoaligning material on each of the first and second mold segments is exposed to the light having a linear polarization. Each layer of photoaligning material is thereby converted into a layer of photoaligned material 611 on the respective mold segment 601, 602.

Figure 11:
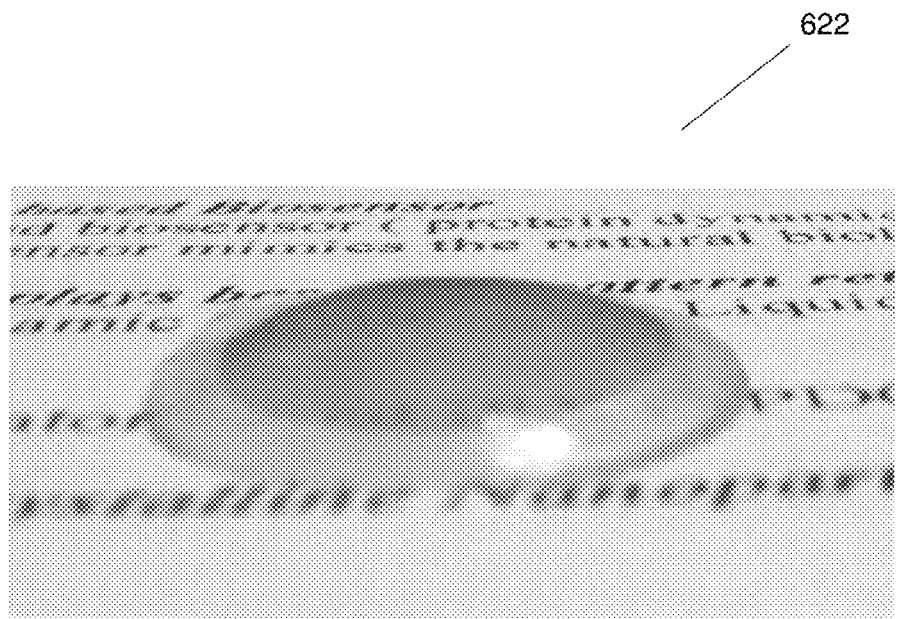
FIG. 11 shows a photo a molded LCP film fabricated using the method illustrated in FIG. 10.

Step (d) comprises arranging the first and second mold segments together to form the cavity and then filling the cavity with the polymerizable liquid crystal. Steps (e) to (g) are then performed to form the LCP film 620 and release the LCP film from the two mold segments 601, 602. FIG. 11 shows an example resulting azobenzene LCP film molded in the form of a spherical lens 622.

A ninth embodiment of the invention provides a method of fabricating a liquid crystal polymer film which is similar to the method of the previous embodiment and will be described with reference to FIG. 10 also.

In this embodiment, step (c) comprises exposing the layer of photoaligning material on the first mold segment 601 to a first linearly polarized light having a first polarization spatial modulation. The layer of photoaligning material on the second mold segment 602 is exposed to a second linearly polarized light having a second polarization spatial modulation, different to the first polarization spatial modulation.

A tenth embodiment of the invention provides a liquid crystal polymer release material comprising three functional groups: a first functional group characterised for photoalignment of liquid crystal materials; a second functional group characterised for solubility in a polar solvent; and a third functional group characterised for adhesion to a substrate material.

Figure 12:
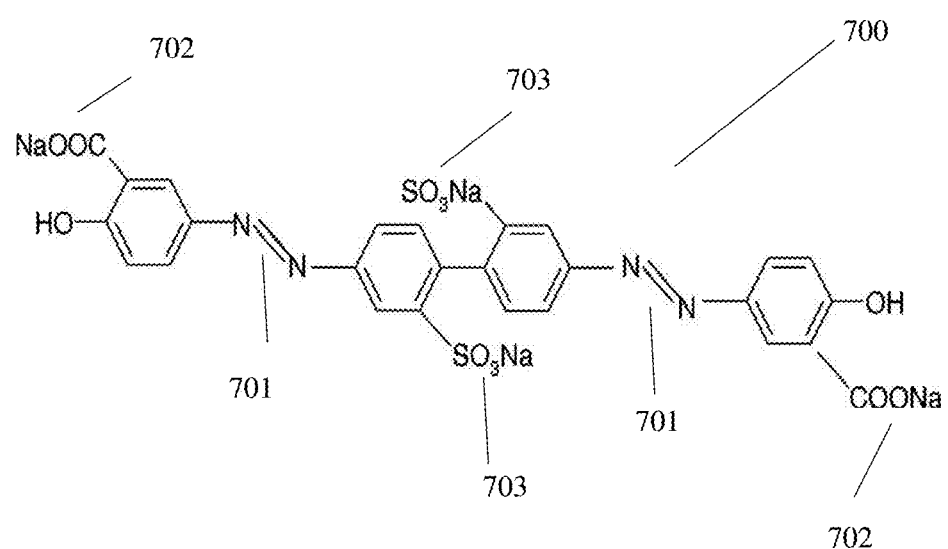
FIG. 12 shows a molecular structure of a liquid crystal polymer release material according to a tenth embodiment of the invention.

FIG. 12 illustrates the molecular structure 700 of sulfonic bisazodye SD1, an azobenzene dye based on chromocentranine R structures which comprise a sulfo group, which is an example of a LCP release material according to this embodiment of the invention.

The LCP release material molecular structure 700 comprises: a first functional group 701 characterised for photoalignment of liquid crystal materials; a second functional group 702 characterised for solubility in a polar solvent; and a third functional group 703 characterised for adhesion to a substrate material. It will however be appreciated that there may not be strict differentiation of the group functionality, and some groups may take part in different functions.

It will be appreciated that the specific orientations used within these FIGURES to demonstrate the apparatus functionality are by way of example only.

The present disclosure is directed to each individual feature, system, material, and/or method described herein. In addition, any combination of two or more such features, systems, materials, and/or methods, if such features, systems, materials, and/or methods are not mutually inconsistent, is included within the scope of the present invention. To avoid undue repetition, not all features are discussed in conjunction with every aspect, embodiment or practice of the disclosure. Features described in conjunction with one aspect, embodiment or practice are deemed to be includable with others absent mutual inconsistency or a clear teaching to the contrary. In some instances, features will be discussed generally rather than in detail in conjunction with a specific aspect, embodiment or practice, and it is understood that such features can be included in any aspect, embodiment or practice, again absent mutual inconsistency or a clear teaching to the contrary.

Those of ordinary skill in the art will readily envision a variety of other means and structures for performing the functions and/or obtaining the results or advantages described herein and each of such variations or modifications is deemed to be within the scope of the present invention. More generally, those skilled in the art would readily appreciate that all parameters, dimensions, materials and configurations described herein are meant to be exemplary and that actual parameters, dimensions, materials and configurations will depend on specific applications for which the teachings of the present invention are used.

Those skilled in the art will recognize or be able to ascertain using no more than routine experimentation many equivalents to the specific embodiments of the invention described herein. It is therefore to be understood that the foregoing embodiments are presented by way of example only and that within the scope of the appended claims, and equivalents thereto, the invention may be practiced otherwise than as specifically described.

In the claims as well as in the specification above all transitional phrases such as "comprising", "including", "carrying", "having", "containing", "involving" and the like are understood to be open-ended. Only the transitional phrases "consisting, of" and "consisting essentially of" shall be closed or semi-closed transitional phrases, respectively, as set forth in the U.S. Patent Office Manual of Patent Examining Procedure §2111.03, 8th Edition, Revision 8. Furthermore, statements in the specification, such as, for example, definitions, are understood to be open ended unless otherwise explicitly limited.

The phrase "A or B" as in "one of A or B" is generally meant to express the inclusive "or" function, meaning that all three of the possibilities of A, B or both A and B are included, unless the context clearly indicates that the exclusive "or" is appropriate (i.e., A and B are mutually exclusive and cannot be present at the same time). "At least one of A, B or C" (as well as "at least one of A, B and C") reads on any combination of one or more of A, B and C, including, for example the following: A; B; C; A & B; A & C; B & C; A & B; as well as on A, B & C.

It is generally well accepted in patent law that "a" means "at least one" or "one or more." Nevertheless, there are occasionally holdings to the contrary. For clarity, as used herein "a" and the like mean "at least one" or "one or more." The phrase "at least one" may at times be explicitly used to emphasize this point. Use of the phrase "at least one" in one claim recitation is not to be taken to mean that the absence of such a term in another recitation (e.g., simply using "a") is somehow more limiting. Furthermore, later reference to the term "at least one" as in "said at least one" should not be taken to introduce additional limitations absent express recitation of such limitations. For example, recitation that an apparatus includes "at least one widget" and subsequent recitation that "said at least one widget is colored red" does not mean that the claim requires all widgets of an apparatus that has more than one widget to be red. The claim shall read on an apparatus having one or more widgets provided simply that at least one of the widgets is colored red. Similarly, the recitation that "each of a plurality" of widgets is colored red shall also not mean that all widgets of an apparatus that has more than two red widgets must be red; plurality means two or more and the limitation reads on two or more widgets being red, regardless of whether a third is included that is not red, absent more limiting explicit language (e.g., a recitation to the effect that each and every widget of a plurality of widgets is red).

ADDITIONAL REFERENCES

[1] N. V. Tabiryan, S. R. Nersisyan, D. M. Steeves and B. R. Kimball, The Promise of Diffractive Waveplates, Optics and Photonics News, 21 (3), 41-45, 2010.
[2] S. R. Nersisyan, N. V. Tabiryan, D. M. Steeves, B. R. Kimball, V. G. Chigrinov, and H.-S. Kwok, Study of azo dye surface command photoalignment material for photonics applications, Appl. Opt. 49 (10), 1720-1727, 2010.
[3] Sarik R. Nersisyan, Nelson V. Tabiryan, Diane M. Steeves, and Brian R. Kimball, characterization of optically imprinted polarization gratings, Appl. Optics 48 (21), 4062-4067, 2009.
[4] H. Sarkissian, B. Zeldovich, N. Tabiryan, "Longitudinally modulated bandgap nematic structure", JOSA B 23, 1712-1717, 2006.

U.S. PATENT DOCUMENTS

| | | |
|---|---|---|
| 4,956,141 | September 1990 | Allen et al. |
| 4,983,332 | January 1991 | Hahn et al. |
| 6,551,531 | April 2003 | Ford et al. |
| 7,094,304 | August 2006 | Nystrom et al. |
| 12/662,525 | April 2010 | Tabirian et al. |

The invention claimed is:

1. A method of fabricating a liquid crystal polymer film, the method comprising:
   (a) providing a support substrate having a surface having a shape arranged to define a form of a liquid crystal polymer film to be fabricated;
   (b) applying a layer of a photoaligning material consisting of an azobenzene, a stilbene, an azoxy, an azomethine, a fulgide or a diarylethene photoresponsive compound in combination with a coating solvent over said surface of said support substrate, said photoaligning material having an absorption band;
   (c) exposing said layer of photoaligning material to a light having a linear polarization and said light comprising a wavelength within said absorption band to convert said layer of photoaligning material into a layer of photoaligned material adapted for aligning molecules of a liquid crystal polymer layer in a predetermined direction;
   (d) applying a layer of a polymerizable liquid crystal over said layer of photoaligned material;
   (e) performing photopolymerization of said layer of polymerizable liquid crystal to form a liquid crystal polymer film of about 1 μm (micrometer) in thickness;
   (f) applying a dissolution solvent to said layer of photoaligned material, said dissolution solvent formulated to dissolve said photoaligned material to thereby release said liquid crystal polymer film from said support substrate; and
   (g) removing said liquid crystal polymer film from said support substrate, said liquid crystal polymer film having a thickness of about 1 μm.

2. A method as claimed in claim 1, wherein said photoresponsive compound has a molecular structure comprising at least one functional group for solubility in a polar solvent.

3. A method as claimed in claim 2, wherein said at least one functional group is a sulfo group.

4. A method as claimed in claim 1, wherein the method comprises, before exposing said layer of photoaligning material to said light, spatially modulating said linear polarization of said light.

5. A method as claimed in claim 4, wherein said linear polarization of said light is spatially modulated with one of a one-dimensional polarization pattern and a two-dimensional polarization pattern.

6. A method as claimed in claim 4, wherein said linear polarization of said light is spatially modulated by transmitting said light through one of a cycloidal diffractive waveplate, a vector vortex waveplate, and an array of vector vortex waveplates.

7. A method as claimed in claim 1, wherein said dissolution solvent is a polar solvent.

8. A method as claimed in claim 1, wherein said dissolution solvent is one of water, Dimethylformamide, and a low molecular weight alcohol.

9. A method as claimed in claim 1, wherein after step (e) the method comprises attaching said liquid crystal polymer film to a carrier substrate, and where step (g) comprises removing said liquid crystal polymer film on said carrier substrate from said support substrate.

10. A method as claimed in claim 9, wherein said liquid crystal polymer film is attached to said carrier substrate by applying a layer of an adhesive onto said liquid crystal polymer film and performing photopolymerization of said layer of said adhesive to form said carrier substrate.

11. A method as claimed in claim 9, wherein said carrier substrate is a polymer film which is thicker and stronger than said liquid crystal polymer film.

12. A method as claimed in claim 9, wherein said liquid crystal polymer film is attached to said carrier substrate by:
   a. applying a layer of an adhesive onto said carrier substrate;
   b. bringing said support substrate and said carrier substrate together to bring said adhesive into contact with said liquid crystal polymer film; and
   c. curing said adhesive.

13. A method as claimed in claim 1, wherein after step (e) the method comprises adhering the liquid crystal polymer film to a second support substrate and the method further comprises, after step (g):
   d. providing a third support substrate carrying a second layer of a photoaligned material and having a second liquid crystal polymer film, different to the first liquid crystal polymer film, provided over said second layer of a photoaligned material; and
   e. applying a second dissolution solvent to said second layer of a photoaligned material, said second dissolution solvent formulated to dissolve said photoaligned material to thereby release said second liquid crystal polymer film from said third support substrate.

14. A method as claimed in claim 13, wherein said first liquid crystal polymer film has a first alignment pattern and said second liquid crystal polymer film has a second alignment pattern, said second alignment pattern being one of a different pattern to said first alignment pattern and a different orientation to said first alignment pattern.

15. A method as claimed in claim 1, wherein said support substrate is a first mold segment and step (a) further comprises providing a second mold segment having a surface having a shape arranged to cooperate with said surface of said first mold segment, said surfaces of said first and second mold segments together defining a cavity defining said shape of said liquid crystal polymer film and wherein step (d) comprises arranging said first and second mold segments together to form said cavity and filling said cavity with said polymerizable liquid crystal.

16. A method as claimed in claim 15, wherein step (b) further comprises applying a layer of said photoaligning material over said surface of said second mold segment and step (c) comprises exposing both said layers of photoaligning material to a light having a linear polarization and said light comprising a wavelength within said absorption band to convert each said layer of photoaligning material into a layer of photoaligned material.

17. A method as claimed in claim 15, wherein step (b) further comprises applying a layer of said photoaligning material over said surface of said second mold segment and step (c) comprises exposing said layer of photoaligning material on said first mold segment to a first linearly polarized light having a first polarization spatial modulation and exposing said layer of photoaligning material on said second mold segment to a second linearly polarized light having a second polarization spatial modulation, different to said first polarization spatial modulation, each said linearly polarized light comprising a wavelength within said absorption band to convert each said layer of photoaligning material into a respective layer of photoaligned material.

18. A method as claimed in claim 1, wherein said polymerizable liquid crystal comprises functional groups, copolymers and additives to control its optical, electro-optical, mechanical, thermodynamic, and chemical properties.

* * * * *